United States Patent [19]

Smith

[11] 4,142,944
[45] Mar. 6, 1979

[54] APPARATUS AND METHODS FOR EFFLUENT STREAM ANALYSIS

[75] Inventor: John L. Smith, Mercerville, N.J.

[73] Assignee: Princeton Applied Research Corporation, Princeton, N.J.

[21] Appl. No.: 872,505

[22] Filed: Jan. 26, 1978

[51] Int. Cl.² .................................................. G01N 27/34
[52] U.S. Cl. ..................................... 204/1 T; 73/61.1 C;
204/195 H
[58] Field of Search .......................... 204/195 H, 1 T;
23/230 R, 253 R; 73/61.1 C

[56] References Cited
FOREIGN PATENT DOCUMENTS 1175463  8/1964  Fed. Rep. of Germany ...... 204/195 H Primary Examiner—G. L. Kaplan
Attorney, Agent, or Firm—Finnegan, Henderson, Farabow & Garrett

[57] ABSTRACT

An effluent delivery tube directs effluent from below mercury drops formed by a mercury drop electrode in a vertically upward direction coaxial to the vertical axis of the mercury drop to provide turbulent free flow of effluent about the drops. A method of analyzing an effluent stream by directing an effluent from below a drop formed by a mercury drop electrode in a vertically upward direction coaxial to the vertical axis of the mercury drop to provide turbulent free flow of effluent about the mercury drop.

9 Claims, 6 Drawing Figures

U.S. Patent   Mar. 6, 1979   Sheet 1 of 3   4,142,944
FIG. 1
FIG. 2
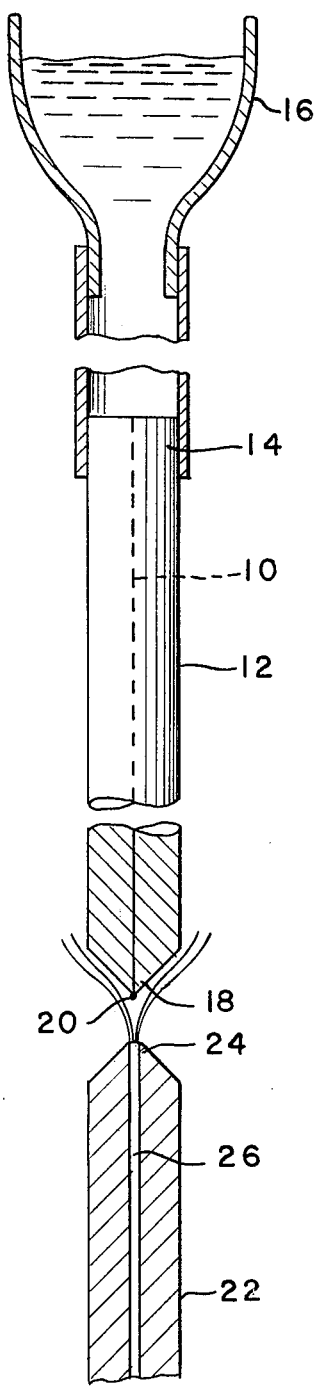
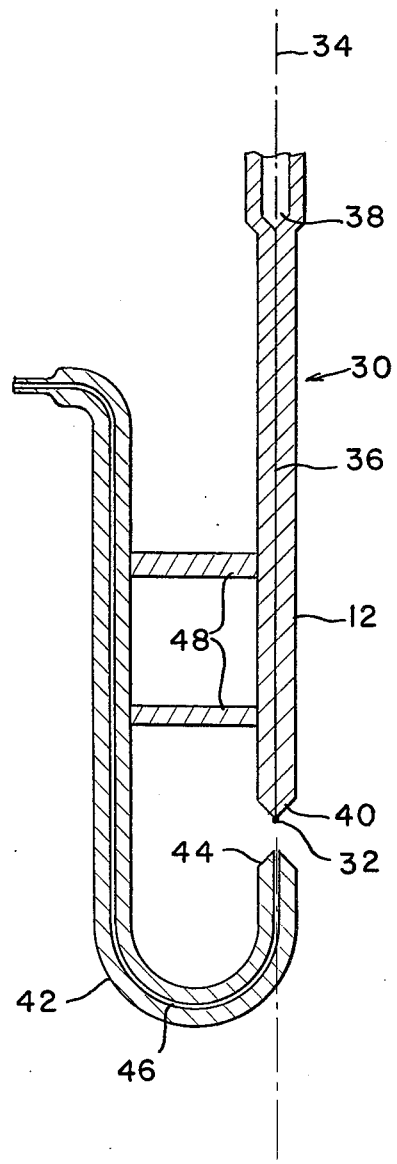

APPARATUS AND METHODS FOR EFFLUENT STREAM ANALYSIS

BACKGROUND

The present invention relates to apparatus and methods for effluent stream analysis and more particularly to apparatus and methods for providing a highly stable and smooth flow of effluent around a measuring electrode.

Polarography, one of a broad class of voltameric techniques, provides chemical analysis of substances in electrolyte solution by the observation of current and voltage relationships of electrodes immersed in the solution. At low voltages, no current flows between the electrodes. However, as the voltage is increased, it becomes great enough for deposition of each reducible substance in solution on the electrodes, and current begins to flow. Generally, the magnitude of the current is proportional to the concentration of the reducible substances in solution and the magnitude of the voltage required to induce this current flow is indicative of the identity of the substance in solution. Thus, precise measurement of the current in the immersed electrodes, as a function of applied potential, provides both qualitative and quantitative analysis of the reducible substances in solution.

Chromatography is a method of separating and analyzing mixtures of chemical substances. A flow of solvent or gas causes the components of the mixtures to migrate differentially in a sorptive media subject to an effluent flow. The time at which the various chemical substances of the mixture emerge from and effluent flow provides an indication of the qualitative content of the substances.

A typical detection apparatus for determining the qualitative content of the substances appearing from the effluent flow may be a form of polarographic detector. Such a polarographic detector consists generally of a variable voltage source, a circuit for measuring current, and an electrolysis cell. The cell typically contains three electrodes immersed in the effluent flow. The three electrodes comprise a reference electrode at which the variable potential is applied, a working or indicating electrode at which current flow is measured, and an auxiliary or counter electrode which regulates the potential between the reference and working electrodes.

The most widely used working or indicating electrode in polarographic detectors is the dropping mercury electrode which consists of a fine bore capillary tube above which a constant head of mercury is maintained. The mercury emerges from the tip of the capillary at the rate of a few milligrams per second and forms spherical droplets at the capillary orifice into the effluent solution at a typical rate of one every two to ten seconds.

The dropping mercury electrode has a number of advantages over other varieties of electrodes. For example, mercury has a high hydrogen overvoltage which allows observation of processes which would normally be obscured by the decomposition of water at other elements. In addition, periodic renewal of the surface area of the dropping mercury electrode minimizes problems due to surface composition changes.

However, the prior art employment of dropping mercury electrodes in liquid chromatographic systems has been severely hampered by (1) an appreciable dead volume existing between the effluent flow and the mercury and (2) by turbulent flow resulting from prior art attempts to minimize the dead volume.

It is accordingly an object of the present invention to provide apparatus and methods for effluent stream analysis wherein the dead volume between the effluent stream and the indicating electrode is minimized. It is a further object of the present invention to provide apparatus and methods for effluent stream analysis wherein a smooth non-turbulent flow is provided around the electrode to maximize sensitivity of analysis.

Additional objects and advantages of the present invention will be set forth in part in the description which follows, and in part will be obvious from the description, or may be learned by practice of the invention. The objects and advantages of the invention may be realized and obtained by means of the instrumentalities and combinations particularly pointed out in the appended claims.

SUMMARY OF THE INVENTION

To achieve the foregoing objects, and in accordance with the purposes of the invention as embodied and broadly described herein, the apparatus for effluent stream analysis of the present invention comprises a mercury drop electrode for forming mercury drops symmetrical about a vertical axis and an effluent delivery mechanism for directing an effluent from below the drops in a vertically upward direction coaxially to the said vertical axis to provide turbulent-free flow of the effluent about the mercury drops.

In a preferred embodiment of the present invention, the mercury drop electrode further includes a capillary and capillary passage having a first end available to receive mercury and a second end at which mercury drops are formed. The second end of the capillary is tapered. Furthermore, in a preferred embodiment of the present invention, the delivery mechanism includes a delivery tube having a tip and a bore through the tip to direct the effluent at the mercury drops. The bore opens directly below the drops and is coaxial with the vertical axis of the tip. The tip is also tapered.

In a preferred embodiment of the present invention a support mechanism is employed for physically attaching the delivery mechanism and the capillary passage one to the other to assure a static and fixed alignment between the bore opening in the delivery tube and the capillary passage.

Still further, a method of analyzing effluent stream in accordance with the present invention and utilizing a mercury drop electrode comprises the steps of forming at the end of a capillary passage mercury drop symmetrical about a vertical axis, and directing an effluent from below the drop in a vertically direction coaxially to the vertical axis of the drop to provide turbulent-free flow of effluent about the mercury drop.

DESCRIPTION OF THE DRAWINGS

A greater appreciation of the objects and advantages of the invention may be understood by the following detailed description taken in conjunction with the drawings, wherein:

FIG. 1 is a sectional diagram of an apparatus for effluent stream analysis in accordance with the teachings of the present invention;

FIG. 2 is another diagram of a preferred embodiment of an apparatus for effluent stream analysis in accordance with the teachings of the present invention;

DETAILED DESCRIPTION

Figure 3:
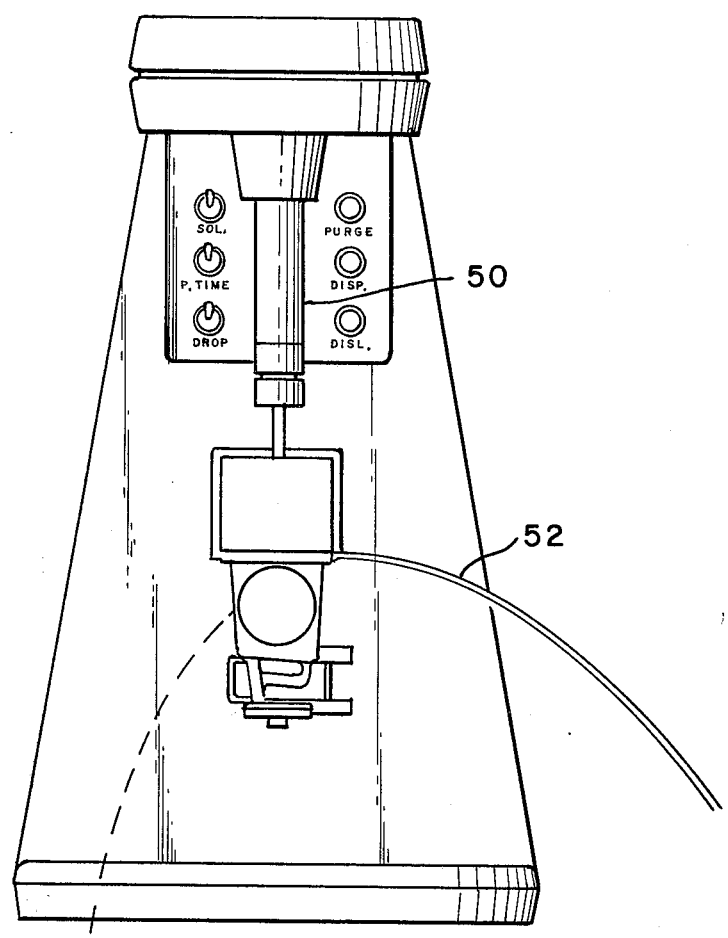
FIG. 3 is a pictorial diagram of one embodiment of a liquid chromatographic detection system employing an apparatus for effluent stream analysis in accordance with the present invention.

Reference will now be made to the present preferred embodiment of the invention, an example of which is illustrated in the accompanying drawings.

Referring to FIG. 1, there is shown a diagram which illustrates an apparatus for effluent stream analysis incorporating the teachings of the present invention.

In accordance with the present invention, an apparatus for effluent stream analysis comprises a mercury drop electrode for forming mercury drops symmetrically about a vertical axis. Such mercury drop electrodes are well known to those skilled in the art and may, for example, comprise a particular variety of mercury drop electrode identified as a static mercury drop electrode and fully described in copending patent application Ser. No. 872,506, filed Jan. 26, 1978, entitled "Static Mercury Drop Electrode" of common assignee herewith.

As is well known to those skilled in the art and illustrated in FIG. 1, a mercury drop electrode includes a capillary passage 10 contained in a fine bore capillary 12. Capillary passage 10 typically has a diameter between the range of 0.003 and 0.012 of an inch for a static mercury drop electrode as illustrated in the afore-identified copending application and typically has an internal diameter of approximately 0.003 of an inch for a standard prior art mercury drop electrode.

In the mercury drop electrode illustrated in FIG. 1, capillary passage 10 has a first end 14 available to receive mercury from a reservoir 16 positioned above first end 14. Furthermore, capillary passage 10 has a second end 18 at which mercury drops 20 are formed. The drops 20, when formed, hang from the second end 18 of capillary 12 in symmetry about a vertical axis through the drops.

In the preferred embodiment of the present invention illustrated in FIG. 1, second end 18 is tapered. This tapering may form, for example, an angle of 45° to the axis of capillary 12.

The apparatus for effluent stream analysis according to the present invention, further includes a delivery means for directing an effluent from below the drops 20 into a vertical upward direction coaxial to the vertical axis of drops 20 to provide turbulent free flow of effluent about the mercury drops.

As illustrated in FIG. 1, the delivery means includes a delivery tube 22 having a tip 24 and a bore 26 through tube 22 and tip 24 to direct effluent at drops 20. The bore 26 opens directly below drops 20 and is coaxial with the vertical axis of the drops 20.

Tip 24 is spaced from the drops 20 a distance preferably within a range of 1.5 to 4 millimeters and may also be tapered. Bore 26 of the effluent delivery means may have an internal diameter on the order ½ millimeter.

In operation of the apparatus for effluent stream analysis illustrated in FIG. 1, mercury in reservoir 16 is allowed to pass through first end 14 of capillary 12 to form drops 20 at the second end 18 of capillary 12. Furthermore, effluent, for example, from the result of liquid chromatographic analysis, is introduced into bore 26 and flows up bore 26 of tube 22 and tip 24 for emergence symmetrically about drop 20. It has been found that effluent emerging from bore 26 flows about drop 20 in a smooth non-turbulent manner thereby providing for an extremely small dead volume and an extremely high level of sensitivity for effluent stream analysis.

It is to be understood that a suitable and known measuring device may be attached to the apparatus illustrated in FIG. 1 to provide electrical analysis of the current appearing at mercury drop 20 and the description of such known apparatus is beyond the scope of this invention, such description being well known to those skilled in the art.

A method of analyzing an effluent stream utilizing a mercury drop electrode in accordance with the teachings of the present invention may also be understood with reference to FIG. 1. The first step of the method is the formation at the end of capillary passage 10 of a mercury drop 20 symmetrical about a vertical axis. A second step of the method is directing an effluent such as in bore 26 from below drop 20 into a vertically upward direction coaxial to the vertical axis of drops 20 to provide turbulent free flow of effluent about mercury drop 20.

It should be understood that the tapering of second end 18 is a significant feature of the present invention which allows the effluent delivery means to provide a turbulent-free flow of effluent about the mercury drop. Experimentation has clearly indicated that use of a flat edge at second end 18 of capillary 12 is totally unsuitable to provide high sensitivity effluent stream analysis. It is only with the employment of a tapered second end 18 that a suitable apparatus is realized.

Another preferred embodiment of the present invention is illustrated in FIG. 2 of the drawings. In FIG. 2, a mercury drop electrode 30 is illustrated for forming mercury drops 32 which are symmetrical about a vertical axis 34. Mercury drop electrode 30 is shown including a capillary passage 36 having a first end 38 available to receive mercury from a reservoir, and a second end 40 at which mercury drops 32 are formed.

In the embodiment of the present invention illustrated in FIG. 2, second end 40 is also tapered at approximately a 45° angle to axis 34. It will be appreciated that second end 40 may be tapered other than at a 45° angle. For example, tapers within a range of 30° to 60° to axis 34 will result in the desired turbulent-free flow of the effluent about mercury drop 32.

As illustrated in FIG. 2, the effluent delivery means of the present invention includes a delivery tube 42 having a tip 44 and a bore 46 extending through tube 42 and tip 44 to direct effluent at drops 32. The bore 46 has an opening directly below drops 32 an is coaxial with vertical axis 34 of drops 32. Tip 44 is spaced below second end 40 a distance similar to that described with reference to the previous embodiment and is also tapered.

As illustrated in FIG. 2, the apparatus for effluent stream analysis of the present invention further includes a support means for physically attaching the delivery means and the capillary passage one to the other to assure static and fixed alignment between the bore opening in the delivery tube and the capillary passage.

More specifically, a support means is illustrated in FIG. 2 as comprising two spacing struts 48 located between tubing 42 and capillary 12. Struts 48 should be of rigid construction and physically attached to both tube 42 and capillary 12. Struts 48 can, for example, be composed of glass or other suitable supporting material. Furthermore, struts 48 should space tube 42 and capillary 12 a sufficient distance apart to enable adjustment of tip 44 into alignment with vertical axis 34 of drops 32.

FIG. 3 illustrates liquid chromatographic detector apparatus employing the apparatus for effluent stream analysis in accordance with the teachings of the present invention. In FIG. 3, a mercury drop electrode 50 is shown positioned above an effluent delivery tube 52.

Figure 4:
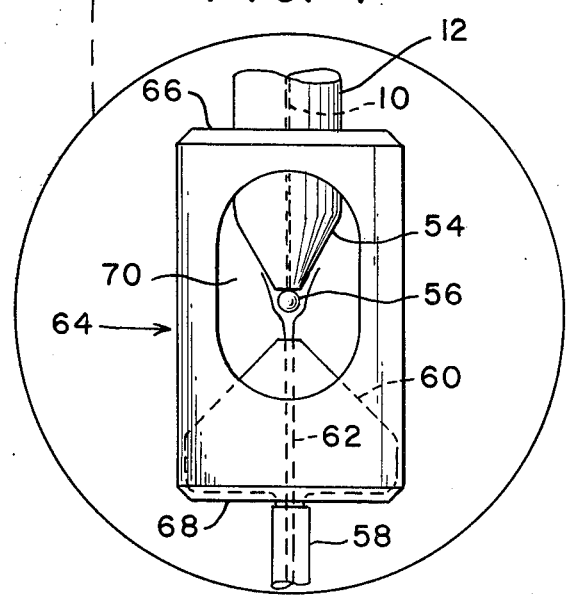
FIG. 4 is an enlargement of one portion of the chromatographic detection system illustrated in FIG. 3.

As more clearly shown in FIG. 4, which is an enlarged view of a portion of FIG. 3, electrode 50 comprises a capillary 12 having a second end 54 at which mercury drops 56 are formed. As further illustrated in FIG. 4, a delivery tube 58 has a tip 60 and a bore 62 through delivery tube 58 and tip 60 to direct effluent at drops 56. Bore 62 is shown opening directly below drops 56 and is coaxial with the vertical axis of symmetry of drops 56. Furthermore, tip 60 is spaced from second end 54 similarly as described with respect to the previous embodiments and is also tapered.

As illustrated in FIG. 4, a support means 64 physically attaches delivery tube 58 and tip 60 of the delivery means of the present invention and capillary passage 10 of capillary 12, one to the other, to assure a static and fixed alignment between the opening of bore 62 and the opening of capillary passage 10 at second end 54 of capillary 12. Support means 64 consists of a cylindrical bushing having a first upper open end 66 and a second lower open end 68. The upper open end 66 of support means 64 is dimensioned to rigidly and fixedly engage second end 54 of capillary 12. The second end 68 of support means 64 is dimensioned to rigidly and fixedly engage tip 60 of the delivery tube means. Furthermore, support means 64 has a plurality of openings or apertures 70 which allow the free passage of fluid into and out of support means 64.

In operation of the embodiment of the present invention illustrated in FIG. 4, effluent exiting bore 62 concentrically surrounds drops 56 to provide a smooth, consistent, non-turbulent flow of effluent over the surface of drops 56. The effluent, after passing drops 56, exits support means 64 through apertures 70. Furthermore, upon dislodgement of drop 56 from capillary 12 by any suitable well-known drop-kick mechanism, drop 56 avoids the opening of bore 62 due to the generally tapered shape of tip 60. Furthermore, mercury drop 56 exits support means 64 through the openings or apertures 70. The exiting of mercury drops 56 from support means 64 through apertures 70 may be facilitated by structuring the taper of tip 60 in a manner whereby drops 56 are encouraged to roll off the taper of tip 60 at the point of contact between tip 60 and openings 70.

Figure 5:
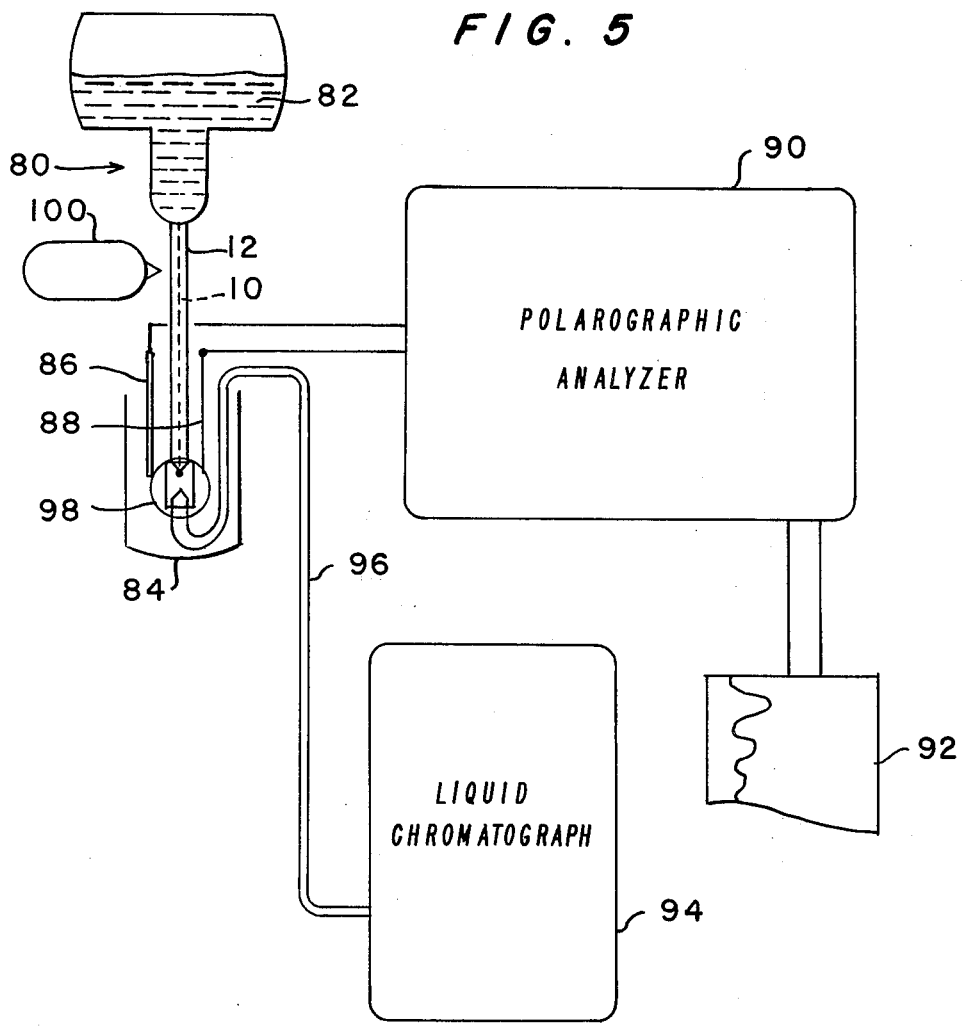
FIG. 5 is a block diagram of a detection system employing the apparatus for effluent stream analysis in accordance with the teachings of the present invention.

A system employing the apparatus for effluent stream analysis in accordance with the present invention is illustrated in FIG. 5.

In FIG. 5, a static mercury drop electrode 80 is shown to include a mercury reservoir 82 and the downwardly extending capillary 12 with an internal fine diameter bore 10. Mercury drop electrode 80 forms a working or indicating electrode of an electrolysis cell 84 which further comprises a reference electrode 86 and a counter or auxiliary electrode 88. As is well known to those skilled in the art, mercury drop electrode 82, reference electrode 86 and counter-electrode 88 are coupled to a polarographic analyzer 90 which produces suitable and well-known analysis of the critical current and voltage relationships of cell 84 and provides as an output of record of these relationships at recorder 92.

FIG. 5 further shows a liquid chromatograph 94 also well known to those skilled in the art, coupled by a delivery tube 96 to an apparatus for effluent stream analysis 98 which is the subject of the present invention. Apparatus 98 is more fully described and depicted in FIG. 4 of the present application. FIG. 5 further includes a drop knock solenoid 100 located adjacent capillary 12 to selectively impart a mechanical thump to capillary 12 which dislodges drops formed at the lower end thereof.

In operation of the system illustrated in FIG. 5, the liquid effluent issuing from liquid chromatograph 94 through delivery tube 96 flows around and engulfs mercury electrode drops 56 at the lower end of capillary 12 in a non-turbulent smooth flow as described above. Analysis of the chemical content of the effluent passing drop 56 is undertaken by polarographic analyzer 90 and recorded on recorder 92 as is well known to those skilled in the art. At any suitable time interval, drop knock solenoid 100 is energized to dislodge drop 56 from the lower end of capillary 12 with drop 56 eventually exiting apparatus 98 and falling into the bottom of cell 84.

The apparatus for effluent stream analysis described above has been found through experimentation to provide an extremely small dead volume on the order of approximately 0.4 microliters which provides substantially increased testing sensitivity over prior art techniques in which dead volume has been known to only approach a minimum of 10 microliters.

Figure 6:
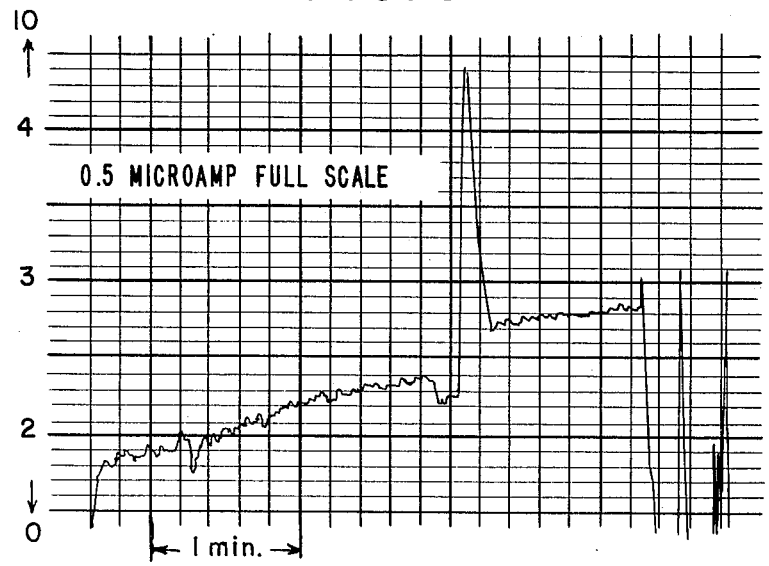
FIG. 6 is a recorder tracing of chromatographic analysis of ascorbic acid in accordance with the teachings of the present invention.

FIG. 6 is a recorded tracing of the liquid chromatograph analysis of 100 nanograms ($10^{-7}$ grams) of ascorbic acid performed using a system similar to that depicted in FIG. 5. The vertical axis of FIG. 6 corresponds to a current with a sensitivity of approximately 50 nanoamperes per inch. The horizontal axis corresponds to a time scale of approximately one minute per inch. This graph is an indication of the extremely high sensitivity which may be obtained using the combination of polarographic analysis and the apparatus for effluent stream analysis of the present invention.

Application exists for detection of compounds exhibiting adsorption or other surface activity on an electrode using the apparatus and methods for effluent stream analysis taught and claimed herein. Using alternating current techniques such as tensammetry, phase sensitive detection, or straight AC voltammetry, it is possible to detect, in a liquid chromatographic effluent or any other flowing systems, compounds such as, but not limited to the following list: enzymes, proteins, tannins, hormones, steroids, colloids, surfactants, detergents, soaps. Under prior art techniques, many of these classes are very difficult to detect with good sensitivity in chromatographic systems. Since adsorption currents are frequently one or two orders of magnitude higher than reduction currents, extremely high sensitivity should be possible in accordance with the teachings of the present invention.

Furthermore, very poorly conducting solutions could be used in the apparatus and methods of the present invention, since only a very thin layer of analyte surrounds the mercury drop and causes a correspondingly small (IR) voltage drop. Potential should be more reproducible, and less potentiostat compliance voltage required, since the counter and reference electrodes may be placed in solutions as conductive as saturated potassium chloride.

The disclosure of U.S. patent application Ser. No. 872,506 filed contemporaneously herewith on Jan. 26, 1978 entitled "Static Drop Mercury Electrode" in the names of John L. Smith and Bruce N. Whitlock and of common assignee herewith is incorporated herein in its entirety by reference thereto as though fully set forth herein.

While particular embodiments of the present invention have been shown and described, it will of course be obvious to one skilled in the art that certain advantages and modifications may be effected without departing from the spirit of the invention, and accordingly, it is intended that the scope of the invention not be determined by the foregoing examples but only by the scope of the appended claims.

What is claimed is:

1. An apparatus for effluent stream analysis comprising:
   a mercury drop electrode for forming mercury drops symmetrical about a vertical axis and including a capillary passage having a first end available to receive mercury and a second end at which said mercury drops are formed, said second end being tapered; and
   an effluent delivery means for directing an effluent from below the drops in a vertically upward direction coaxial to said vertical axis to provide turbulent free flow of effluent about the mercury drops, said delivery means including a delivery tube having a tip and a bore through said tip to direct said effluent at said drops, said bore opening directly below said drops and coaxial with said vertical axis, said tip being tapered.

2. The apparatus for effluent stream analysis recited in claim 1 including support means for physically attaching said delivery means and said capillary passage one to the other to assure a static and fixed alignment between said bore opening and said capillary passage.

3. The apparatus for effluent stream analysis recited in claim 2 wherein said bore of said effluent delivery means has an internal diameter on the order of one half millimeter.

4. An apparatus for effluent stream analysis comprising:
   a mercury drop electrode for forming mercury drops symmetrical about a vertical axis and including a capillary passage having a first end available to receive mercury and a second end at which said mercury drops are formed, said second end being tapered; and
   an effluent delivery means for directing an effluent from below the drops for flow in a vertically upward direction coaxial to said vertical axis to provide turbulent free flow of effluent about the drops.

5. The apparatus for effluent stream analysis recited in claim 4 wherein said mercury drop electrode includes means for forming static mercury drops.

6. A method of analyzing an effluent stream utilizing a mercury drop electrode comprising the steps of
   forming at the end of a capillary passage a mercury drop symmetrical about a vertical axis;
   directing an effluent from below the drop in a vertically upward direction coaxial to the vertical axis to provide turbulent free flow of effluent about the mercury drop.

7. A method according to claim 6 including forming a static mercury drop at the end of the capillary passage.

8. A method according to claim 6 including flowing the effluent through the bore at a velocity on the order of 40 cm/sec at a flow rate on the order of 5 ml/min.

9. A method according to claim 6 including flowing mercury through a capillary passage toward the end thereof to form the drop, flowing effluent through a bore to direct the effluent concentrically about the mercury drop, and maintaining the passage and bore in fixed static relation one to the other.

* * * * *